United States Patent [19]

Seidman

[11] Patent Number: 5,977,162
[45] Date of Patent: *Nov. 2, 1999

[54] THERAPEUTIC TREATMENT FOR AUDITORY FUNCTION

[76] Inventor: Michael D. Seidman, 5310 Putman, West Bloomfield, Mich. 48323

[*] Notice: This patent issued on a continued prosecution application filed under 37 CFR 1.53(d), and is subject to the twenty year patent term provisions of 35 U.S.C. 154(a)(2).

[21] Appl. No.: 08/931,134

[22] Filed: Sep. 16, 1997

Related U.S. Application Data

[60] Provisional application No. 60/026,162, Sep. 16, 1996.

[51] Int. Cl.$^6$ ............... A61K 31/385; A61K 31/205
[52] U.S. Cl. ............................... 514/440; 514/556
[58] Field of Search ..................... 514/440, 556

[56] References Cited

U.S. PATENT DOCUMENTS

| | | | |
|---|---|---|---|
| 4,135,790 | 1/1979 | Takahashi et al. | 350/357 |
| 4,193,670 | 3/1980 | Giglia et al. | 350/357 |
| 4,293,194 | 10/1981 | Takahashi | 350/357 |
| 4,313,648 | 2/1982 | Yano et al. | 350/166 |
| 4,325,611 | 4/1982 | Huggins et al. | 350/357 |
| 4,350,414 | 9/1982 | Takahashi et al. | 350/357 |
| 4,585,312 | 4/1986 | Ishiwata et al. | 350/357 |
| 4,664,934 | 5/1987 | Ito et al. | 427/38 |
| 4,775,227 | 10/1988 | Silver | 350/357 |
| 4,824,221 | 4/1989 | Endo et al. | 350/357 |
| 4,935,934 | 6/1990 | Ferrand et al. | 372/41 |
| 4,962,504 | 10/1990 | Aubert et al. | 372/41 |
| 5,011,582 | 4/1991 | Oshikawa et al. | 204/140 |
| 5,124,822 | 6/1992 | Becker et al. | 359/58 |
| 5,140,604 | 8/1992 | Alablanche et al. | 372/41 |
| 5,148,306 | 9/1992 | Yamada et al. | 359/271 |
| 5,188,902 | 2/1993 | Lin | 428/426 |
| 5,202,788 | 4/1993 | Weppner | 359/270 |

FOREIGN PATENT DOCUMENTS

| | | |
|---|---|---|
| 0 628 849 A1 | 12/1994 | European Pat. Off. . |
| 57-081241 | 5/1982 | Japan . |

OTHER PUBLICATIONS

Ames, B.N. Dietary Carcinogens and Anticarcinogens. Oxygen Radicals and Degenerative Diseases. Science. 221(4617):1256–64, Sep. 23, 1983.

Bast A and Haenen GR. Interplay between Lipoic Acid and Glutathione in the Protection Against Microsomal Lipid Peroxidation. Biochimica et Biophysica Acta. 963(3):558–61. Dec. 16, 1988.

Devasagayam TP, Subramanian M, Pradhan DS, Sies H. Prevention of Singlet Oxygen–Induced DNA Damage by Lipoate. Chemico–Biological Interactions. 86(1):79–92. Jan. 1993.

Dimpfel W, Spuler M, Pierau FK, Ulrich H. Thiotic Acid Induces Dose–Dependent Sprouting of Neurites in Cultured Rat Neuroblastoma Cells. Dev. Pharmacol. Ther. 14(3):193–99. 1990.

Fariello RG et al, Systemic Acetyl–L–Carnitine Elevates Nigral Levels of Glutathione and GABA. Life Sci. 43:289–292. 1988.

Fujii T, Kuraishi M and Satoh M. Specific Binding Sites for Bifemelane in the Hippocampus of the Guinea Pig, Relevant to its Pharmacological Actions. Neuropharmacology 30:1291–1995. 1991.

Gadaleta MN, Petruzella V, Daddabbo L, Olivieri C, Fracasso F, Loguercio Polosa P, Cantatore P. Mitochondrial DNA Transcription and Translation in Aged Rat. Effect of Acetyl–L–Carnitine. Ann. NY Acad. Sci. 717:150–160. 1994.

Gersdorff M, Franceschi D. Intérêt du Piracétam Dans le Traitement de la Surdité Brusque Idiopathique. Ann. Oto–Laryng. (Paris) 103:283–285. 1986.

Giurgea C and Mouravieff–Lesuisse F. Pharmacological Studies on an Elementary Model of Learning—The Fixation of an Experience at Spinal Level: Part I: Pharmacological Reactivity of the Spinal Cord Fixation Time. Arch. int. Pharmacodyn. 191:279–291. (1971).

Harman D. Nutritional Implications of the Free–Radical Theory of Aging. Journal of the American College of Nutrition. 1(1):27–34. 1982.

Harman D. Free Radical Theory of Aging: Effect of Free Radical Reaction Inhibitors on the Mortality Rate of Male LAF Mice. Journal of Gerontology. 23(4):476–82. Oct. 1968.

Harman D. The Aging Process. Proceedings of the National Academy of Sciences of the USA. 78(11):7124–8. Nov. 1981.

Heidrick ML, Hendricks LC, Cook DE. Effect of Dietary 2–Mercaptoethanol on the Life Span, Immune System, Tumor Incidence and Lipid Peroxidation Damage in Spleen Lymphocytes of Aging BC3F$_1$ Mice. Mechanisms of Aging & Development. 27(3):341–58. Oct. 31, 1984.

Herrmann WM and Stephan K. Efficacy and Clinical Relevance of Cognition Enhancers. Alzheimer Disease and Associated Disorders 5:S7–S12. 1991.

Imperato A, Ramacci MT, Angelucci L. Acetyl–L–Carnitine Enhances Acetylcholine Release in the Striatum and Hippocampus of Awake Freely Moving Rats. Neurosci. Lett. 107:251–255. 1989.

Kabes J, Erban L, Hanzlicek L and Skondia V. Biological Correlates of Piracetam Clinical Effects in Psychotic Patients. J. Int Med. Res. 7:277–283. 1979.

(List continued on next page.)

*Primary Examiner*—Theodore J. Criares
*Attorney, Agent, or Firm*—Gifford, Krass, Groh, Sprinkle, Anderson & Citkowski, P.C.

[57] ABSTRACT

A nutritional supplement for enhancing mitochondrial function in cells includes 10–1000 mg of alpha-lipoic acid, 10–1000 mg acetyl-L-carnitine, 15–360 mg coenzyme Q-10, and 15–360 mg glutathione. The composition may further comprise a carrier for these components such as a liquid or tablet for oral ingestion on a daily basis.

14 Claims, No Drawings

OTHER PUBLICATIONS

Kagan VE, Shvedova A, Serbinova E, Khan S, Swanson C, Powell R, Packer L. Dihydrolipoic Acid—A Universal Antioxidant Both in the Membrane and in the Aqueous Phase. Reduction of Peroxyl, Ascorbyl and Chromanoxyl Radicals. Biochem. Pharmacol. 44:1637–1649. 1992.

Markowska AL, Olton DS. Dietary Acetyl–L–Carnitine Improves Spatial Behaviour of Old Rats. Int. J. Clin. Pharmacol Res. 10:65–68. 1990.

Orlando G, Milano S, Ramacci MT and Angelucci L. Effect of Acetyl–L–Carnitine Chronic Treatment on Discrimination Models in Aged Rats. Physiology & Behavior, 44:769–773. 1988.

Paradies G, Ruggiero FM, Pestrosillo G, Gadaleta MN, Quagliariello E. Effect of Aging and Acetyl–L–Carnitine on the Activity of Cytochrome Oxidase and Adenine Nucleotide Translocase in Rat Heart Mitochondria. FEBS Lett. 350:213–215. 1994.

Passeri M, Cucinotta D, Bonati PA, Iannuccelli M, Parnetti L and Senin U. Acetyl–L–Carnitine in the Treatment of Mildly Demented Elderly Patients. Int. J. Clin Pharm. Res. X(1/2):75–79. 1990.

Sapolsky R, Armanini M, Packan D, Tombaugh G. Stress and Glucocorticoids in Aging. Endocrinol. Metab. Clin. North Am. 16(4):965–980. 1987.

Scholich H, Murphy ME, Sies H. Antioxidant Activity of Dihydrolipoate Against Microsomal Lipid Peroxidatin and Its Dependence on Alpha–Tocopherol. Biochimica et Biophysica Acta. 1001(3):256–61. Feb. 20, 1989.

Serbinova E, Khwaja S, Reznick AZ, Packer L. Thioctic Acid Protects Against Ischemia—Reperfusion Injury in the Isolated Perfused Langendorff Heart. Free Radic. Res. Comm. 17(1):49–58, 1992.

Suzuki YJ, Tsuchiya M, Packer L. Lipoate Prevents Glucose–Induced Protein Modifications. Free Radical Res. Comm. 17(3):211–217. 1992.

Suzuki YJ, Tsuchiya M, Parker L. Thioctic Acid and Dihydrolipoic Acid are Novel Antioxidants which Interact with Reactive Oxygen Species. Free Radc. Res. Comm. 15:255–263. 1991.

Tolmasoff JM, Ono T, Cutler RG. Superoxidase Dismutase: Correlation with Life–Span and Specific Metabolic Rate in Primate Species. Proceedings of the National Academy of Sciences of the USA. 77(5):2777–81. May 1980 UCB, SA 1966.

Vernon MW and Sorkin EM. Piracetam. An Overview of its Pharmacological Properties and a Review of its Therapeutic Use in Senile Cognitive Disorders. Drugs & Aging, 1:17–35. 1991.

Wolthuis OL. Experiments with UCB 6215, A Drug which Enhances Acquisition in Rats: Its Effects Compared with Those of Metamphetamine. Eur. J. Pharm., 16:283–297. 1971.

The Reactions of Some Lanthanide Oxides with Liquid Lithium article from the *Journal of the Less–Common Metals*, 64 (1979) pp. 115–125,.

Low temperature phase transitions in $RbDy(MoO_4)_2$ and $Kdy(WO_4)_2$, article from *Brief Communications*, pp. 381–383, Sov. J. Low Temp. Phys. 4(6), Jun. 1978.

Preparation and Properties of Double Metaphosphates of Rare Earths and Lithium, N. N. Chudinova and N. V. Vinogradova, pp. 1706–1710, original article submitted Jun. 25, 1978.

Les Éléments Des Terres Rares, *Colloques Internationaux De Centre National De La Recherche Scientifique*, Paris–Grenoble, 5–10 Mai 1969.

Rare Earth Research II, Proceedings of the Third Conference on Rare Earth Research, Apr. 21–24, 1963, Preparation and Structure of Some Mixed Lithium Rare Earth Compounds, Karl S. Vorres, pp. 147–151.

*Condensed Matter*, Coexistence of valence fluctuating and stable PR ions in $Pr_6O_{11}$, E. Holland–Moritz, Original received Apr. 27, 1992, revised version Jun. 25, 1992, pp. 285–288.

*Journal of Luminescence* 1,2 (1970), Some Considerations on Rare–Earth Activated Phosphors, pp. 766–777,.

Publication, *Electrical Conductivity and Oxygen Vacancy Mobility in CaO–DOPED Yitrium Oxide*, original article submitted, Sep. 23, 1986, published Jan. 1989, S. Volchenkova and D.S. Zubankova, pp. 66–70.

*Journal of Solid State Chemistry*, Simultaneous Measurements of Oxygen pressure, Composition, and Electrical Conductivity in Praseodymium Oxides: II. $Pr_{10}O_{18}$ and $PrO_{2-x}$ Phases, 1983, pp. 111–120.

*Rare Earths No. 8*, 1986. 3, The Rare Earth Society of Japan. *Journal of Solid State Chemitry 50*, Simultaneous Measurements of Oxygen Pressure, Composition, and Electrical Conductivity of Praseodymium Oxides: I. $Pr_7O_{12}$ and $Pr_9O_{16}$Phases, (1983), pp. 100–110.

*J. inorg. nucl. Chem. vol. 43, No. 11*, Crystal Data for Rare Earth Orthophosphates of the Monazite Structure–Type, 1981, pp. 2807–2809.

*Journals of Alloys and Compounds 192*, The binary higher oxides of the rare earths, 1993, pp. 57–63.

*Journals of Alloys and Compounds, 192*, Phase Transitions: $Pr_7O_{12} \rightarrow \sigma-PrO_x \rightarrow A-Pr_2O_3$ of Pr oxide thin film and the phase boundaries, 1993, pp. 90–92.

*Sov. Phys. Crystallogr. 24(3)*, Triclinic modification of lithium–rare earth tungstates $LiLn(WO_4)_2$, where Ln is La—Sm, May–Jun. 1979, pp. 258–263.

*New Frontiers in Rare Earth Science and Applications*, Proceedings of the International Conference on Rare Earth Development and Applications vol. I, Optical Spectra, Energy Levels and Crystal–Field Analysis Of $Pr^{3+}$, $Nd^{3+}$, $Er^{3+}$, In Li, K $LnP_4O_{12}$ Crystals, Beijing, The People's Republic of China, Sept. 10–14, 1985, pp. 345–346.

Publication, *Calculation of the Thermodynamic Characteristics of Some Compounds of Rare–Earth Elements*, 1978, pp. 265–267.

*Russian Journal of Physical Chemistry*, 56(1), The Ionic Conductivity of Alkali Metal Lanthanum Tungstates $Mla(WO_4)_2$ (M=Li, Na, or K), 1982, pp. 123–124.

*Contribution from the Noves Chemical Laboratory, University of Illinois*, Observations on the Rare Earths. LXII.[1] Some Observations on Solutions of Certain Rare Earth Metal Salts in Basic Solvents, Therald Moeller and Paul A. Zimmerman, received Jan. 14, 1953, pp. 3940–3943.

*Communications of the American Ceramic Society*, Investigation of the Phase Diagram for the Pseudobinary System $Li_2SO_4$–$La_2(SO_4)_3$ and Its Ionic Conductivity, Oct. 1988, pp. C–436–C–438.

*Rare Earth Spectroscopy, Proceedings of the International Symposium on RareEarths Spectroscopy*, Spectroscopic Properties of $KPr_xY_{1-x}P_4O_{12}$ Crystals, Michael Malinowski, Sep. 10–15, 1994, pp. 348–353.

*Inorganica Chimica Acta*, 140, Preparation and Characterization of $La_2Li_{0.5}Al_{0.5}O_4$ with $K_2NiF_4$ Structure*, F. Abbattista†, M. Vallino and D. Mazza, 1987, pp. 147–149.

*Journal of Solid State Chemistry 70,* Lithiated Rare–Earth Thiospinels and Selenospinels*†, Pablo de la Mora‡ and John B. Goodenough§, 1987, pp. 121–128.

*Fine Chemical for the Electronics Industry II Chemical Applications for the 1990's,* Rare Earths in the Electronics Industry, K. A. Gschneidner, Jr., 1991, pp. 63–94.

Chemical Abstracts 106:14804j (Cavallini et al), 1987.

Chemical Abstracts 109:122463t (Geremia et al), 1988.

Chemical Abstracts 116:99245g (Qian et al), 1992.

Chemical Abstracts 117:143128t (Prehn et al), 1992.

Chemical Abstracts 120:45784w (Stoll et al), 1994.

THERAPEUTIC TREATMENT FOR AUDITORY FUNCTION

This application claims the benefits of U.S. Provisional application Ser. No. 60/026,162 filed Sep. 16, 1996.

FIELD OF THE INVENTION

This invention relates generally to methods and compositions for supplementing nutritional intake, and in particular, to methods and compositions for supplementing nutritional intake in such a way so as to enhance mitochondrial function. Most specifically, the present invention relates to a nutritional supplement containing alpha-lipoic acid, acetyl-L-carnitine, coenzyme Q-10, and glutathione.

BACKGROUND OF THE INVENTION

Aging is a progressive accumulation of metabolic and physiologic changes associated with an increasing susceptibility to disease. Several explanations for the aging process are described in the contemporary literature. Among the most prominent is the dysdifferentiation hypothesis of aging and the membrane hypothesis of aging. The dysdifferentiation hypothesis proposes that aging is the result of a continued programmed differentiation leading to either a cessation of normal gene activity or a systematic activation of genes whose effects are deleterious to cellular function. Conversely, the membrane hypothesis of aging (MHA) states that aging is related to decreasing effectiveness of cellular protective and reparative mechanisms secondary to damage from oxygen radicals. This yields biochemical and metabolic errors, which progressively accumulate, resulting in cell aging and ultimately death. Therefore the MHA suggests that reactive oxygen metabolite (ROM) induced cell membrane structural damage is the primary mediator in cellular aging.

Reactive oxygen metabolites, also known as free oxygen radicals (FOR) are the putative initiators in the membrane hypothesis of aging. ROMs are a normal by-product of oxidative phosphorylation, and are also formed under conditions of ischemia, hypoperfusion and because of environmental contaminants. Among the many detrimental activities of ROM, or free oxygen radicals, is direct damage to mitochondrial DNA (mtDNA). Progressive accumulation of mtDNA damage renders cells unable to conduct oxidative phosphorylation reactions effectively, thereby leading to a bioenergetically deficient cell. Over time, mitochondrial DNA damage accumulates and leads to cellular dysfunction with subsequent organ failure, aging and ultimately death. This sequence forms the basis of the MHA. Additionally, there is evidence of a reduction in the oxidant-protective enzymes superoxide dis-mutase and catalase associated with aging. Thus not only are there increases in the deleterious effects of ROMs, but there is a reduction in the enzymes and mitochondrial metabolites necessary for protection from ROM and for effective mitochondrial function.

There is increasing support in the literature that reactive oxygen metabolites and mitochondrial dysfunction may initiate processes that lead to Alzheimer's disease, non-specific dementias and cognitive disorders. Thus, compounds that increase mitochondrial function and scavenge or block the activities of reactive oxygen metabolites may slow or even reverse the processes of these disorders.

Variation in life spans of certain mammalian and plant species is in part dependent upon free radical scavenging systems. It has been observed that animals with longer life spans had higher levels of SOD activity. Many studies have investigated dietary increases in antioxidants and have demonstrated life span increases by 13–30%.

α-lipoic acid

α-lipoic acid is a coenzyme for the pyruvate dehydrogenase complex in the mitochondrial matrix. It is an essential cofactor for metabolism in α-ketoacid dehydrogenase reactions. This vitamin-like substance has been supplemented orally for health benefits and has also been used as a therapeutic agent in a variety of hepatic and neurological disorders, as well as mushroom poisoning. Consideration has also been given to the use of α-lipoic acid in the treatment of diabetes mellitus and atherosclerosis, in which decreased levels of α-lipoic acid have been found. Interestingly, a specific 10.4 kb mitochondrial DNA deletion has been found in patients with diabetes mellitus and sensorineural hearing loss. Thus, it may also be hypothesized that patients with these disorders as well as aging might benefit from a diet supplemented with lipoic acid. Dietary supplementation of α-lipoic acid successfully prevents myocardial damage induced by ischemia-reperfusion injury. Presently its primary therapeutic use is for the treatment of diabetic polyneuropathy.

In physiological systems, α-lipoic acid usually exists as lipoamide covalently attached to lysine residue of the enzyme complexes. It functions in the transfer of the two-carbon fragment from α-hydroxyethylthiamin pyrophosphate to acetyl-CoA, and it gets reduced in the process. The reduced form of α-lipoic acid is dihydrolipoic acid (DHLA) containing a disulfihydral structure. DHLA has been found to exert some antioxidant actions. It has been shown to prevent microsomal lipid peroxidation by reducing glutathione which in turn recycles vitamin E. DHLA has also been demonstrated to be a free oxygen radical scavenger to reduce peroxyl, ascorbyl and chromanoxyl radicals, and to inhibit singlet oxygen.

Acetyl L-carnitine

Acetyl L-carnitine is the acetyl ester of carnitine, a biological compound which plays a key role in the transport of fatty acids from the cytosol into the mitochondrial matrix of B-oxidation. Acetyl L-carnitine modulates, through regulation of acetyl Co-A intracellular concentration, the metabolisms of sugars, lipids and amino acids, this way playing a pivotal role in cellular energy and turn over of cell membranes and proteins. Observations demonstrating a positive effect on survival were recently made on some rat populations treated with acetyl L-carnitine. The mechanisms of such an effect are currently unknown, but they are very similar to the survival observed in rats fed a restricted caloric diet. Chronic treatment with acetyl L-carnitine has shown enhanced stimulation of antiperoxidative systems, antagonism of the age-related effect on glucocorticoid secretion, increase in acetylcholine release and improvement in learning and memory. It has been reported that aged rat brain and heart possessed a reduced steady state level of mitochondrial transcripts due to reduced RNA synthesis. Pretreatment of senescent rats with acetyl L-carnitine was able to bring back the levels of mitochondrial transcripts to adult levels in a time and dose-dependent function.

Acetyl L-carnitine is capable of restoring the integrity of the cardiac mitochondrial membrane altered by aging (specifically the cardiolipin content), thereby restoring the normal activity of cytochrome oxidase, adenine nucleotide translocase, and phosphate carrier. This allows more efficient oxidative phosphorylation, and therefore, improves cardiac performance in aged animals.

Coenzyme Q-10

Coenzyme Q-10 (CoQ-10) is an important mitochondrial precursor and is essential in the transduction of energy.

Reduced CoQ-10 functions as an antioxidant and can therefore combat the production of free oxygen radicals. There is evidence supporting an age-related decline of CoQ-10 in humans and other species, thus further supporting the membrane hypothesis of aging. CoQ-10 is currently used alone or in combination as a health/nutritional supplement. However, there is evidence suggesting that long-term supplementation of this precursor alone has no beneficial effect on lifespan or energy production. However, it is believed that when combined with acetyl L-carnitine and lipoic acid, cellular degeneration is limited and energy production is enhanced.

Glutathione

Glutathione (L-gamma-glutamyl-L-cysteinyl-glycine; GSH) is an endogenous thiol that detoxifies reactive oxygen species. It is also involved in the metabolism and detoxification of xenobiotics, drugs and their metabolites and offers protection from oxidizing ROM via reactions catalyzed by GSH-S-transferase, transpeptidases, transhydrogenases, and peroxidases and reductases. Mitochondrial glutathione is critical to cell viability, and the glutathione redox cycle is a primary antioxidant defense system within the mitochondrial matrix. Additional functions include intracellular binding, transport of lipophilic substances and prostaglandin synthesis.

Many studies have demonstrated that alterations of glutathione levels through excess or reduced production have a beneficial or harmful influence in cellular function, respectively. Specifically, it has been shown that sulfhydryl compounds reduce gentamicin induced outer hair cell damage in vitro and that gentamicin ototxicity, in vivo, may be reduced using glutathione, and diethyldithiocarbamate offers protection from cisplatin ototoxicity. Conversely, systemic inhibition of glutathione synthesis potentiates the ototoxicity of a combination of ethacrynic acid and kanamycin, and cisplatin rephrotoxicity is potentiated by GSH depletion. It has also been shown that the mechanism for toxicity of certain clinically used drugs occurs secondary to reduced glutathione levels with an increase in reactive oxygen species. Recent studies have demonstrated an 86% age-associated reduction in glutathione levels in the auditory nerve while other cochlear tissues have had stable levels.

Studies of patients with Alzheimer's disease have demonstrated age-dependent decreases of glutathione-peroxidase activities and their cofactors. Additionally, there was a significant increase in plasma glutathione peroxidase which was interpreted as an imbalance between reactive oxygen species and peripheral antioxidant opposing forces. These findings were not observed in controls. Other enzyme changes have been studied, including glutathione reductase, catalase and superoxide dismutase in patients with Alzheimer's disease. The findings demonstrated significantly elevated enzyme activity levels where lipid peroxidation was most prevelent, as documented with levels of thiobarbituric acid. It is believed that there is a compensatory elevation in antioxidant activity in response to increased free radical formation.

Piracetam

Piracetam ($C_6H_{10}N_2O_2$) is a nootropic compound which exhibits cognition-enhancing properties possibly through a potentiation of neurotransmission, although the formal mechanism has not been established. Piracetam possesses a very low toxicity and lacks serious side-effects. This compound has been used in several clinical and experimental conditions including: the treatment of motion sickness, protection of hypoxia-induced amnesia and enhancement of acquisition in passive avoidance experiments with rats. In general, piracetam seems to be somewhat effective in patients with mild to moderate dementia, Alzheimer's disease, Parkinson's disease and in the psychotic state schizophrenics. Additionally, complete recovery of sudden deafness has been shown with piracetam. Piracetam demonstrates an ability to increase systemic and microvascular circulation possibly because of decreased platelet aggregation, enhancement of red blood cell deformability and adherence of erythrocytes to endothelial cells. Piracetam has been shown to increase the survival rate of rats subjected to hypoxia and also to decrease the time of recovery from hypoxia. Piracetam is absorbed very well after oral administration with a 100% bioavailability. It is excreted practically unchanged in the urine and completely eliminated after thirty hours.

These compounds together will synergistically act against the processes of cellular degradation through their antioxidant properties and their ability to upregulate mitochondrial function, as well as other physiologic and biochemical actions. The nutritional supplement of the present invention overcomes the limitations of the prior art in that it utilizes the synergistic combination of nutritionally effective amounts of the above-referenced compounds to enhance mitochondrial function. These and other advantages of the present invention will be readily apparent from the description, discussion and experimental examples which follow.

SUMMARY OF THE INVENTION

There is disclosed herein a nutritional supplement for enhancing mitochondrial function. The supplement comprises nutritionally effective amounts of at least two components selected from the group consisting of lipoic acid, acetyl-L-carnitine, coenzyme Q-10, and glutathione. In a preferred embodiment, the lipoic acid comprises alpha-lipoic acid. In one embodiment, the supplement further comprises piracetam.

In particular embodiments, the alpha-lipoic acid comprises 10–1000 mg, and the acetyl-L-carnitine comprises 10–1000 mg. The coenzyme Q-10 comprises 15–360 mg, and the glutathione comprises 15–360 mg. The nutritional supplement of the present invention is preferably taken on a daily basis.

The composition may further comprise a carrier for these components such as a liquid or tablet. The nutritional supplement of the present invention may also include ancillary ingredients such as colorings, flavorings and the like, as is known in the art.

DETAILED DESCRIPTION OF THE INVENTION

The present invention is directed to a nutritional supplement for enhancing the mitochondrial function of cells. The supplement of the present invention enhances mitochondrial function which will physiologically and biochemically enhance energy production on a cellular level. This increased energy production will likely benefit people who exercise at capacity, such as athletes or individuals who exercise frequently, but will also be of benefit to individuals with relatively sedentary lifestyles. Additionally, as we know that mitochondrial function and energy production decline with cellular degeneration associated with the normal aging process, this product will also counteract some of the biochemical processes associated with cellular degradation. Specifically, it may offer benefits to patients with cognitive disorders such as non-specific dementias and potentially Alzheimer's disease.

In the broadest sense, the present invention is directed to a nutritional supplement comprising the synergistic combination of a mitochondrial metabolite and a cofactor. In one embodiment, a nootropic agent may be used instead of a cofactor.

In one embodiment, the mitochondrial metabolite comprises lipoic acid, specifically alpha-lipoic acid. The mitochondrial metabolite may also comprise acetyl-L-carnitine and/or glutathione. A preferred cofactor comprises coenzyme Q-10. The nootropic agent may comprise piracetam.

In a preferred embodiment of the invention, the composition comprises 10–1000 mg of alpha-lipoic acid, more specifically 100 mg. The composition also comprises 10–1000 mg acetyl-L-carnitine, more specifically 100 mg. The invention further comprises 15–360 mg coenzyme Q-10, more specifically 60–180 mg, most specifically 60–120 mg. The invention also comprises 15–360 mg glutathione, more specifically 60–180 mg, most specifically 60–120 mg. Preferably, the nutritional supplement of the present invention is taken once a day. If piracetam is utilized, it comprises 100–800 mg, more specifically 300 mg, preferably taken twice a day.

Preferably, the nutritional supplement of the present invention is administered on a daily basis. In order to obtain the synergistic effects of the components, they may be suspended in a carrier such as a liquid or tablet, as is known in the art, and ingested orally. Ancillary ingredients such as colorings and flavorings may be added, as is well known in the art.

The present invention is illustrated in the following experimental example.

Experiment

The study of auditory sensitivity and mitochondrial DNA deletions in three separate treatment groups in twenty-four month old animals was conducted. A control group was fed a regular diet, and two treatment groups existed for the use of acetyl-L-carnitine and lipoic acid (100 mg/kg body weight/day). Auditory sensitivity was studied using the auditory brainstem response testing. Animals were then randomly assigned to one of the three groups. After one month of treatment the subjects' hearing were retested, the animals were sacrificed, and muscle, brain and cochlear tissues were harvested. Findings indicate a statistically significant improvement in hearing in the acetyl-L-carnitine group at 6,9,12 and 18 kHz compared to the control group ($p<0.05$). This effect was not seen at 3 kHz ($p=0.07$). Lipoic acid protected hearing at 3 kHz only ($p<0.05$) and although a trend was seen at the other test frequencies, the findings were not statistically significant. Preliminary studies regarding the mitochondrial DNA revealed less bright band patterns in both of the treated groups compared to the control subjects. These findings suggest several mechanisms: 1) An actual therapeutic effect of repair in the existing mitochondria, as there appears qualitatively to be fewer deletions in the treated groups; or 2) The possibility for newly generated wild type (normal) mtDNA; or 3) A combination of the two processes.

The data points from the auditory brain response test are tabulated below and which can be graphed:

|  | pre 3 kHz | post 3 kHz | pre 6 kHz | post 6 kHz | pre 9 kHz | post 9 kHz | pre 12 kHz | post 12 kHz | pre 18 kHz | post 18 kHz |
| --- | --- | --- | --- | --- | --- | --- | --- | --- | --- | --- |
| ctrl 1 | 65 | 65 | 60 | 65 | 65 | 75 | 65 | 75 | 75 | 75 |
| ctrl 2 | 45 | 55 | 50 | 60 | 45 | 55 | 55 | 60 | 50 | 60 |
| ctrl 3 | 60 | 70 | 70 | 70 | 60 | 70 | 65 | 70 | 75 | 75 |
| ctrl 4 | 50 | 50 | 60 | 65 | 45 | 50 | 50 | 60 | 50 | 55 |
| ctrl 5 | 65 | 75 | 65 | 65 | 70 | 75 | 65 | 60 | 75 | 75 |
| ctrl 6 | 55 | 65 | 60 | 70 | 65 | 65 | 55 | 60 | 65 | 65 |
| ctrl 7 | 60 | 70 | 60 | 75 | 70 | 75 | 75 | 70 | 75 | 80 |
| ALCAR 1 | 55 | 55 | 55 | 45 | 65 | 60 | 60 | 60 | 60 | 50 |
| ALCAR 2 | 50 | 55 | 60 | 50 | 65 | 55 | 60 | 55 | 65 | 60 |
| ALCAR 3 | 60 | 60 | 55 | 55 | 45 | 55 | 50 | 45 | 55 | 60 |
| ALCAR 4 | 60 | 50 | 60 | 50 | 55 | 50 | 60 | 50 | 50 | 50 |
| ALCAR 5 | 65 | 65 | 45 | 50 | 45 | 45 | 50 | 40 | 55 | 50 |
| ALCAR 6 | 40 | 40 | 50 | 45 | 40 | 45 | 45 | 40 | 45 | 40 |
| LA 1 | 55 | 55 | 65 | 60 | 65 | 65 | 70 | 75 | 65 | 70 |
| LA 2 | 60 | 50 | 50 | 60 | 60 | 65 | 65 | 55 | 55 | 60 |
| LA 3 | 55 | 55 | 50 | 55 | 45 | 50 | 55 | 50 | 60 | 65 |
| LA 4 | 55 | 50 | 60 | 50 | 65 | 55 | 50 | 55 | 50 | 50 |
| LA 5 | 65 | 60 | 60 | 55 | 55 | 60 | 65 | 70 | 75 | 65 |
| LA 6 | 60 | 65 | 55 | 55 | 65 | 70 | 55 | 60 | 65 | 70 |

It will be appreciated from the foregoing that a nutritional supplement for enhancing mitochondrial function in cells may be prepared from the synergistic combination of a mitochondrial metabolite such as alpha-lipoic acid, acetyl-L-carnitine, and/or glutatione, and a cofactor such as coenzyme Q-10.

The foregoing discussion and examples are merely meant to illustrate particular embodiments of the invention, and are not meant to be limitations upon the practice thereof. It is the following claims, including equivalents, which cope of the invention.

I claim:

1. A composition comprising at least two components in synergistic synergistic effective amounts to promote auditory sensitivity selected from the group consisting of:
   190–1000 mg lipoic acid,
   10–1000 mg acetyl-L-carnitine,
   15–500 mg coenzyme Q-10, and
   15–500 mg glutathione.

2. The supplement of claim 1 and further comprising a carrier for said components.

3. The supplement of claim 1 wherein said lipoic acid comprises alpha-lipoic acid.

4. The supplement of claim 2 wherein said carrier comprises a liquid.

5. The supplement of claim 2 wherein said carrier comprises a tablet.

6. The supplement of claim 1 wherein said coenzyme Q-10 comprises 60–180 mg.

7. The supplement of claim 1 wherein said coenzyme Q-10 comprises 60–120 mg.

8. The supplement of claim 1 wherein said glutathione comprises 60–180 mg.

9. The supplement of claim 1 wherein said glutathione comprises 60–120 mg.

10. The supplement of claim 1 further comprising piracetam, wherein said piracetam comprises 100–800 mg.

11. The supplement of claim 10 wherein said piracetam comprises 300 mg.

12. A supplement for promoting auditory sensitivity comprising:

150 mg alpha-lipoic acid, 150 mg acetyl-L-carnitine, 60 mg coenzyme Q-10, and 30 mg glutathione.

13. A method of promoting auditory sensitivity auditory cells, said method comprising the step of:

administering to said cells a composition comprising at least two components in synergistic effective amounts at least two components selected from the group consisting of 10–1000 mg lipoic acid, 10–1000 mg acetyl-L-carnitine, 15–500 mg coenzyme Q-10, and 15–500 mg glutathione.

14. The method of claim 13 wherein said step of administering takes place daily.

* * * * *

UNITED STATES PATENT AND TRADEMARK OFFICE
CERTIFICATE OF CORRECTION

PATENT NO. : 5,977,162
DATED : November 2, 1999
INVENTOR(S) : Michael D. Seidman It is certified that error appears in the above-identified patent and that said Letters Patent are hereby corrected as shown below:

Column 3, line 30 - Replace "ototxicity" with --ototoxicity--.
Column 3, line 35 - Replace "rephrotoxicity" with --nephrotoxicity--.
Column 6, line 52 - Delete "synergistic" (second occurrence).
Column 6, line 54 - Replace "190" with --10--.
Column 8, line 3 - Insert --in-- after "sensitivity".

Signed and Sealed this

Third Day of April, 2001

Attest:

NICHOLAS P. GODICI

*Attesting Officer*   Acting Director of the United States Patent and Trademark Office